US009504731B2

(12) United States Patent
Nishibori et al.

(10) Patent No.: US 9,504,731 B2
(45) Date of Patent: Nov. 29, 2016

(54) THERAPEUTIC AGENT, TREATMENT METHOD AND INSPECTION METHOD FOR DISEASES CAUSED BY ACTIVATION OF NEUTROPHILS

(71) Applicant: National University Corporation Okayama University, Okayama-shi (JP)

(72) Inventors: Masahiro Nishibori, Okayama (JP); Shuji Mori, Okayama (JP); Hidenori Wake, Okayama (JP); Hideo Takahashi, Okayama (JP); Keyue Liu, Okayama (JP); Kiyoshi Teshigawara, Okayama (JP); Masakiyo Sakaguchi, Okayama (JP)

(73) Assignee: National University Corporation Okayama University, Okayama-shi (JP)

( * ) Notice: Subject to any disclaimer, the term of this patent is extended or adjusted under 35 U.S.C. 154(b) by 0 days.

(21) Appl. No.: 14/406,191

(22) PCT Filed: May 28, 2013

(86) PCT No.: PCT/JP2013/064779
§ 371 (c)(1),
(2) Date: Dec. 5, 2014

(87) PCT Pub. No.: WO2013/183494
PCT Pub. Date: Dec. 12, 2013

(65) Prior Publication Data
US 2015/0141322 A1 May 21, 2015

(30) Foreign Application Priority Data
Jun. 6, 2012 (JP) ................. 2012-129232

(51) Int. Cl.
*A61K 38/00* (2006.01)
*C07K 9/00* (2006.01)
*A61K 38/17* (2006.01)
*G01N 33/68* (2006.01)

(52) U.S. Cl.
CPC ........... *A61K 38/1709* (2013.01); *A61K 38/00* (2013.01); *G01N 33/6893* (2013.01); *G01N 2800/067* (2013.01); *G01N 2800/125* (2013.01); *G01N 2800/26* (2013.01)

(58) Field of Classification Search
None
See application file for complete search history.

(56) References Cited

U.S. PATENT DOCUMENTS

| | | | |
|---|---|---|---|
| 7,205,392 B2 | 4/2007 | Olsson et al. | |
| 7,662,388 B2 | 2/2010 | Welsh et al. | |
| 2005/0042201 A1 | 2/2005 | Olsson et al. | |
| 2016/0146835 A1* | 5/2016 | Kuroda | G01N 33/6893 435/7.94 |

FOREIGN PATENT DOCUMENTS

| | | |
|---|---|---|
| JP | 2004-527242 A | 9/2004 |
| JP | 2007-528710 A | 10/2007 |
| WO | 2011123041 A1 | 10/2011 |

OTHER PUBLICATIONS

Shannon et. al. Blood, Sep. 30, 20i0, vol. 116, No. 13.*
Shannon et al. Blood, Sep. 30, 2010, vol. 116, No. 13.*
Vu et al. Journal of Biological Chemistry, vol. 286, No. 35, 2011, p. 30314-30323.*
Czura et al. J. Infect Dis. (2003) 187 (Supplement 2): S391-S396.* Rheologic.*
Wake et al. EBioMedicine, 2016, vol. 9, pp. 180-194.*
International Search Report mailed Jul. 23, 2013 in International Application No. PCT/JP2013/064779.
Kirschenbaum, Linda et al., "Importance of Platelets and Fibrinogen in Neutrophil-endothelial Cell Interactions in Septic Shock," Critical Care Medicine, 2004, vol. 32, No. 9, pp. 1904-1909.
Poon, Ivan K.H. et al., "Histidine-rich Glycoprotein: The Swiss Army Knife of Mammalian Plasma," Blood, 2011, vol. 117, No. 7, pp. 2093-2101.
Rydengard, Victoria et al., "Histidine-rich Glycoprotein Protects from Systemic Candida Infection," PLOS Pathogens, 2008, vol. 4, No. 8, pp. E1000116.
Shannon, Oonagh et al., "Histidine-rich Glycoprotein Promotes Bacterial Entrapment in Clots and Decreases Mortality in Mouse Model of Sepsis," Blood, 2010, vol. 116, No. 13, pp. 2365-2372.

(Continued)

*Primary Examiner* — Jeanette Lieb
(74) *Attorney, Agent, or Firm* — Kilyk & Bowersox, P.L.L.C.

(57) ABSTRACT

The present invention provides a therapeutic agent, a treatment method and an inspection method for diseases caused by activation of neutrophils. More specifically, the invention relates to a neutrophil activation regulator which comprising a histidine-rich glycoprotein (HRG) as an active ingredient, and provides a therapeutic agent for diseases caused by neutrophil activation comprising the neutrophil activation regulator, a treatment method for diseases caused by neutrophil activation, and further an inspection method for diseases caused by neutrophil activation. The present invention is based on the neutrophil activation regulator including the HRG as an active ingredient. The present invention extends to the depressant agent for neutrophil-vascular endothelial cell interaction including the HRG of the present invention as an active ingredient, the treatment method for diseases caused by neutrophil activation and/or inflammatory diseases accompanied by neutrophil activation. The present invention also extends to the inspection method for inflammatory diseases accompanied by neutrophil activation by measuring the blood HRG level.

10 Claims, 19 Drawing Sheets

(56) References Cited

OTHER PUBLICATIONS

Tsuchida-Straeten, N. et al., "Enhanced Blood Coagulation and Fibrinolysis in Mice Lacking Histidine-rich Glycoprotein (HRG),"Journal of Thrombosis and Haemostasis, 2005, vol. 3, No. 5, pp. 865-872.

Vu, Trang T. et al., "Histidine-rich Glycoprotein Binds Fibrin(ogen) with High Affinity and Competes with Thrombin for Binding to the Gamma'-chain," Journal of Biological Chemistry, 2011, vol. 286, No. 35, pp. 30314-30323.

Extended European Search Report issued in corresponding European Patent Application No. 13801138.2 dated Feb. 10, 2016 (10 pages).

Manderson et al., "Interactions of histidine-rich glycoprotein with immunoglobulins and proteins of the complement system," Molecular Immunology, vol. 46, 2009, pp. 3388-3398.

* cited by examiner

FIG. 1
Purification of the HRG from human plasma
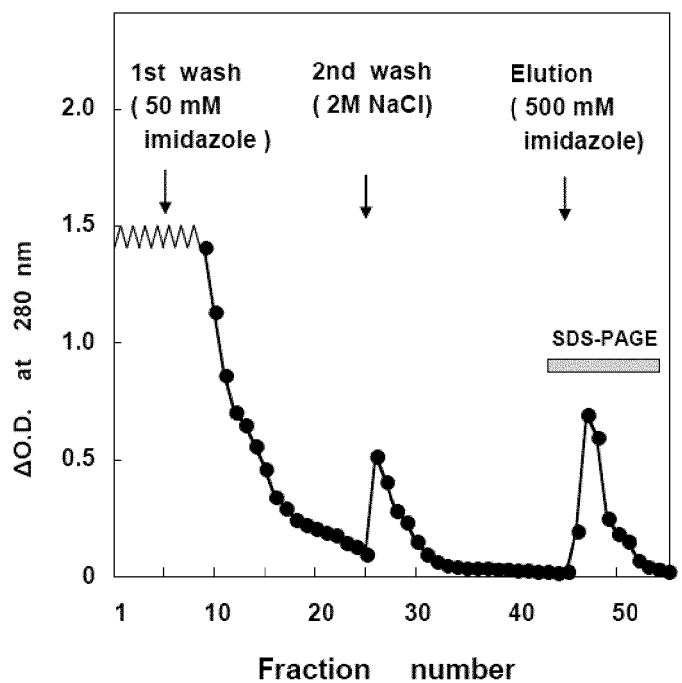
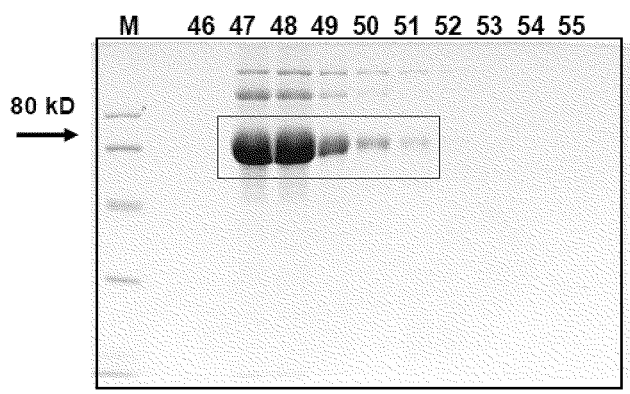

FIG. 2
Purification of the HRG from human
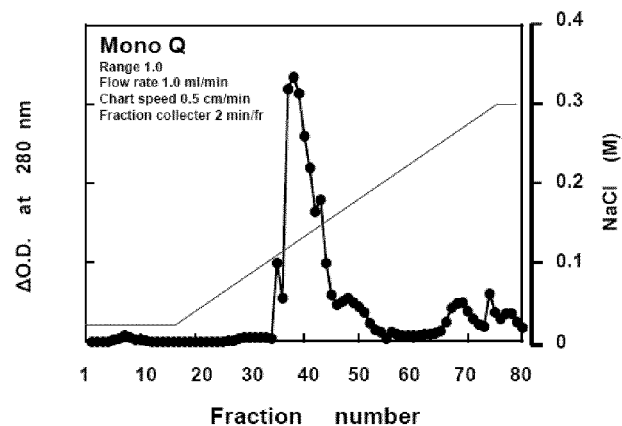
↓
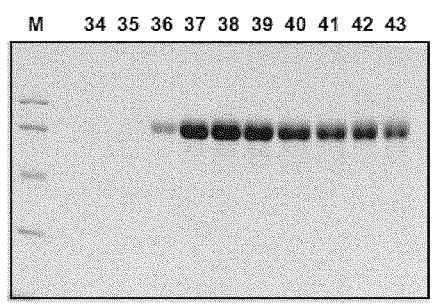
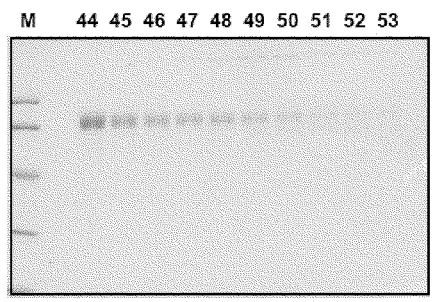

Neutrophil activation regulator (HRG:1μM)

The HRG did not enhance horizontal migration.

Positive control (fMLP : 1μM)

Horizontal migration was enhanced.

FIG. 5

Observation of morphological change of the neutrophil by an electron microscope

Human neutrophil suspension
(5 × 10⁵ cells / 50 μl of ice cold HBSS)
↓
Add the sample (50 μl)
HRG (160 μg/ml, 2 μM)
HBSS
fMLP (2 μM)
↓
Incubation at 37°C for 0, 2 and 15 minutes
↓
Add a cooled 2% glutaraldehyde (0.1 M phosphate buffered saline (pH 7.4))
↓
Mixing
↓
Treatment with a fixing solution at 4°C for 12 hours
↓
Observation of the morphology of the neutrophil by an an electron microscope FIG. 11
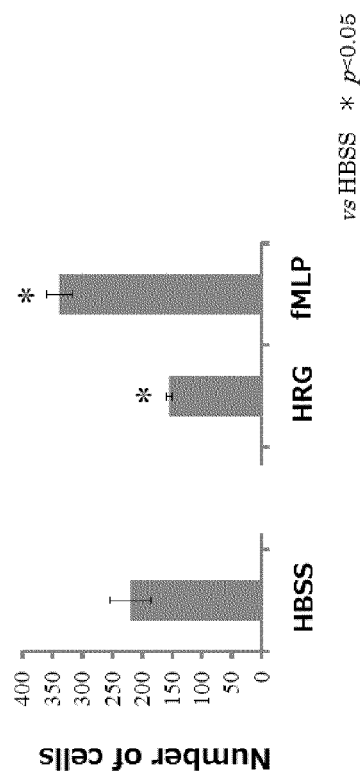
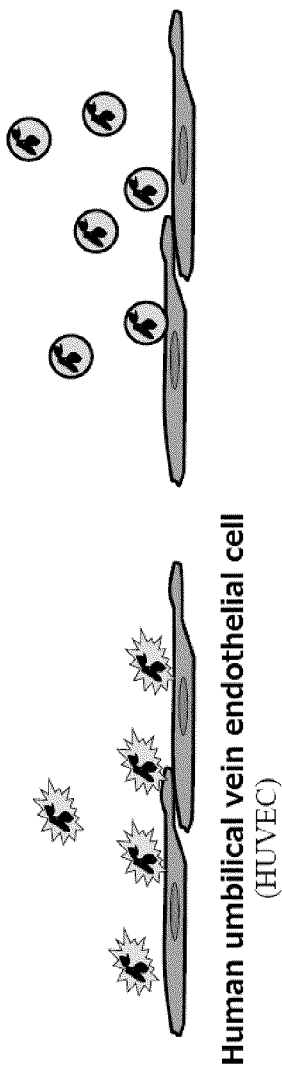

THERAPEUTIC AGENT, TREATMENT METHOD AND INSPECTION METHOD FOR DISEASES CAUSED BY ACTIVATION OF NEUTROPHILS

CROSS-REFERENCE TO RELATED APPLICATIONS

This application is the National Phase of International Patent Application No. PCT/JP2013/064779, filed May 28, 2013, which claims priority to Japan Application No. 2012-129232, filed Jun. 6, 2012. The contents of these applications are herein incorporated by reference in their entirety.

TECHNICAL FIELD

The present invention relates to a therapeutic agent, a treatment method and an inspection method for diseases caused by activation of neutrophils. More specifically, the invention relates to an agent for neutrophil activation regulator which comprising a histidine-rich glycoprotein (hereinafter, may also be simply referred to as "HRG") as an active ingredient, and relates to a therapeutic agent for diseases caused by neutrophil activation comprising the neutrophil activation regulator, a treatment method for diseases caused by neutrophil activation, and further an inspection method for diseases caused by neutrophil activation measuring the HRG.

The present application claims priority of Japanese Patent Application No. 2012-129232, which is incorporated herein by reference.

BACKGROUND ART

Blood includes erythrocytes, leukocytes and platelets as cell components. Among them, the leukocytes are classified into five categories: granulocytes (neutrophil, eosinophil and basophil), lymphocytes and monocytes. The neutrophils are the greatest number of cell types in human, and are well known to function on the front line of biological defense against bacterial infection, histological damage, and the like. The neutrophils are activated by bacterial cell components (e.g. lipopolysaccharide: LPS), bacteria-derived peptide, complement C5a, IL-8, and the like. The neutrophil is one of main ingredients of granulocytes in leucocytes, and when a foreign substance like bacteria enters a living body, the neutrophil migrates to its site and phagocytizes a foreign substance such as bacteria to generate active oxygen. Furthermore, the neutrophil plays an important role in release of bactericidal proteins such as lysozyme and defensin (degranulation) and elimination of foreign substances by actions of the proteins as well as various acidic hydrolase, or the like. However, if this active oxygen and the bactericidal proteins are excessively released outside the cells, they cause tissue damages, and optionally worsen an acute inflammation caused by entrance of foreign substances. Furthermore, in cases of particular diseases such as acute pulmonary disorder, acute respiratory distress syndrome and other neutrophil-related inflammations, this action of the neutrophil is known to have adverse effects on diseases.

Neutrophil elastase is a neutral protease having a molecular weight of about 30,000 and present in azurophil granule (lysosome). In a physiological state, in the neutrophil, the neutrophil elastase digests and degrades a phagocytized bacterium and foreign substance, and on the outside of the neutrophil, degrades elastin, collagen (types III and IV), fibronectin, immunoglobulin, blood coagulation factor XIII, etc. to regulate tissue biosynthesis. When the neutrophil elastase is excessively released and inhibitors such as α1-AT (α1-antitrypsin) are deficient, it may degrade even biological constituents and cause its own tissue damage. In inflammation, the neutrophil infiltrates into an inflammatory lesion, but conversely there is an aspect in which inflammation is caused by a substance produced by leucocyte like elastase. Recently, particularly in clinical sites, the kinetics of the neutrophil elastase and various diseases have attracted attentions. The neutrophil elastase has potent and broad degradation ability for proteins, and since it degrades particularly collagen, elastin, proteoglycan, etc. which are extracellular matrix components, it had been considered as one of factors of histological damages. Thus, medicines focusing to inhibitory effects of the neutrophil elastase are being developed. For example, there is a report that an H2 receptor antagonist, ranitidine hydrochloride (Name of drug: Zantac) decreases an intracellular $Ca^{2+}$ concentration of the neutrophil and reduces release of the neutrophil elastase. In addition, sivelestat sodium (Name of drug: Elaspol) is a specific inhibitor for elastase released from the neutrophil out of the cell, and also a therapeutic agent which has a license to be applied to respiratory distress syndrome and acute pulmonary disorder in Japan. These drugs are not essentially drugs which inhibit activation of the neutrophil, but work on only one factor released by the activated neutrophil to inhibit its enzyme activity, and thus its anti-inflammatory action is expected.

Although there is a report about a substance which acts on a factor released an activated neutrophil and inhibits its activity as mentioned above, an inhibitory mechanism of the neutrophil is largely unknown. Particularly, for preventing runaway activation of the neutrophil in the circulation, the neutrophil should be kept in an inactive state. However, there has been no report about a factor capable of maintaining/regulating the neutrophil in an inactive state.

HRG (Histidine-rich glycoprotein) is a plasma protein with a molecular weight of about 80 kDa which was identified by Heimburger et al. in 1972. HRG is a high histidine-containing protein made up of a total of 507 amino acids in which 66 histidines are contained, and is mainly synthesized in a liver and contained in human plasma at a concentration as extremely high as about 100-150 μg/ml. HRG is known to be involved in regulation of a coagulation fibrinolysis system and control of angiogenesis (Non Patent Literature 1). Furthermore, a method for inhibiting angiogenesis by administration of a HRG polypeptide, and a pharmaceutical composition and a product which comprising the HRG polypeptide, an antibody and receptor binding to the HRG polypeptide, a HRG-deficient plasma and polynucleotide, a HRG polypeptide-coding vector and a host cell are disclosed (Patent Literature 1). Additionally, in relation to the field of angiogenesis, there is a disclosure relating to the use of a substantially-pure continuous polypeptide with an anti-angiogenesis activity containing a subfragment derived from a central area of the HRG (Patent Literature 2).

However, there has been no report about effects of the HRG on control of the neutrophil.

CITATION LIST

Non Patent Literature

[NPL 1] Blood, Vol. 117, No. 7, 2093-2101 (2011)

Patent Literature

[PTL 1] JP2004-527242A
[PTL 2] JP2007-528710A

SUMMARY OF INVENTION

Technical Problem

An object of the present invention is to provide a therapeutic agent, a treatment method and an inspection method for diseases caused by neutrophil activation. Furthermore, an object of the present invention is to provide a depressant agent for neutrophil-vascular endothelial cell interaction comprising a neutrophil activation regulator, and a therapeutic agent for diseases caused by neutrophil activation and/or inflammatory diseases accompanied by neutrophil activation.

Solution to Problem

As a result of earnest investigations for solving the above-mentioned problems, the inventors of the present application have found that the HRG has a function for controlling neutrophil activities, and have completed the present invention related to the neutrophil activation regulator including the HRG as an active ingredient. The present invention extends to the depressant agent for neutrophil-vascular endothelial cell interaction including the HRG as an active ingredient, the therapeutic agent for diseases caused by neutrophil activation and/or inflammatory diseases accompanied by neutrophil activation, and the treatment method using such a therapeutic agent, and furthermore to the inspection method for inflammatory diseases accompanied by neutrophil activation by measuring the blood HRG level.

Namely, the present invention is made up of the followings.

1. A neutrophil activation regulator comprising a HRG as an active ingredient.
2. The neutrophil activation regulator described in the preceding item 1, wherein the regulation of neutrophil activation is inhibition of neutrophil activation.
3. A depressant agent for neutrophil-vascular endothelial cell interaction, comprising the neutrophil activation regulator described in the preceding item 1 or 2.
4. A therapeutic agent for diseases caused by neutrophil activation and/or inflammatory diseases accompanied by neutrophil activation, comprising the neutrophil activation regulator described in the preceding item 1 or 2.
5. The therapeutic agent described in the preceding item 4, wherein the diseases caused by neutrophil activation and/or the inflammatory diseases accompanied by neutrophil activation are one or a plurality of diseases selected from sepsis, acute respiratory distress syndrome, acute pancreatitis, acute pulmonary disorder, pulmonary disorder caused by the hemorrhagic shock, multiple organ failure, burn, multiple injury, idiopathic interstitial pulmonary fibrosis, cerebral trauma, spinal cord injury, neuropathic pain, cerebral infarction, cerebral vasospasm after the subarachnoid hemorrhage, epilepsy, status epilepticus, viral encephalitis, influenza-associated encephalopathy, inflammatory bowel disease, kawasaki disease, multiple sclerosis, diabetic vascular complication, hepatitis, arteriosclerosis, asthma bronchial, chronic bronchitis, pulmonary emphysema, organ dysfunction after surgical operation, organ dysfunction after radiotherapy, nephritis, nephrotic syndrome, acute renal failure, haemodialysis, extracorporeal circulation, artificial breathing, acute/chronic rejection after organ transplantation, SLE, rheumatoid arthritis, DIC, autoimmune disease group, Behcet's disease, myocarditis, endocarditis, ischemia reperfusion disorder, myocardial infarction, congestive heart failure, adipose tissue inflammation, neutrophilic dermatosis, Sweet's disease, Stevens-Johnson syndrome, Reye syndrome, cachexia, chronic fatigue syndrome and fibromyalgia.
6. The therapeutic agent described in the preceding item 4 or 5, wherein the diseases caused by neutrophil activation and/or the inflammatory diseases accompanied by neutrophil activation are diseases selected from sepsis, acute respiratory distress syndrome, acute pancreatitis and acute pulmonary disorder.
7. A therapeutic method for diseases caused by neutrophil activation and/or inflammatory diseases accompanied by neutrophil activation, wherein the neutrophil activation regulator comprising the HRG as an active ingredient is used.
8. The therapeutic method described in the preceding item 7, wherein the diseases caused by neutrophil activation and/or the inflammatory diseases accompanied by neutrophil activation are one or a plurality of diseases selected from sepsis, acute respiratory distress syndrome, acute pancreatitis, acute pulmonary disorder, pulmonary disorder caused by the hemorrhagic shock, multiple organ failure, burn, multiple injury, idiopathic interstitial pulmonary fibrosis, cerebral trauma, spinal cord injury, neuropathic pain, cerebral infarction, cerebral vasospasm after the subarachnoid hemorrhage, epilepsy, status epilepticus, viral encephalitis, influenza-associated encephalopathy, inflammatory bowel disease, kawasaki disease, multiple sclerosis, diabetic vascular complication, hepatitis, arteriosclerosis, asthma bronchial, chronic bronchitis, pulmonary emphysema, organ dysfunction after surgical operation, organ dysfunction after radiotherapy, nephritis, nephrotic syndrome, acute renal failure, haemodialysis, extracorporeal circulation, artificial breathing, acute/chronic rejection after organ transplantation, SLE, rheumatoid arthritis, DIC, autoimmune disease group, Behcet's disease, myocarditis, endocarditis, ischemia reperfusion disorder, myocardial infarction, congestive heart failure, adipose tissue inflammation, neutrophilic dermatosis, Sweet's disease, Stevens-Johnson syndrome, Reye syndrome, cachexia, chronic fatigue syndrome and fibromyalgia.
9. The therapeutic method described in the preceding item 7 or 8, wherein the diseases caused by neutrophil activation and/or the inflammatory diseases accompanied by neutrophil activation are diseases selected from sepsis, acute respiratory distress syndrome, acute pancreatitis, and acute pulmonary disorder.
10. An inspection method for diseases caused by neutrophil activation and/or inflammatory diseases accompanied by neutrophil activation, wherein a blood HRG level is measured.
11. The inspection method described in the preceding item 10, wherein the blood HRG level is measured by an immunological procedure.
12. The inspection method described in the preceding item 10, wherein the diseases caused by neutrophil activation and/or the inflammatory diseases accompanied by neutrophil activation are one or a plurality of diseases selected from sepsis, acute respiratory distress syndrome, acute pancreatitis, acute pulmonary disorder, pulmonary disorder caused by the hemorrhagic shock, multiple organ failure, burn, multiple injury, idiopathic interstitial pulmonary fibrosis, cerebral trauma, spinal cord injury, neuropathic pain, cerebral infarction, cerebral vasospasm after the subarachnoid hemorrhage, epilepsy, status epilepticus, viral encephalitis, influenza-associated encephalopathy, inflammatory bowel disease, kawasaki disease, multiple sclerosis, diabetic vascular complication, hepatitis, arteriosclerosis, asthma bronchial, chronic bronchitis, pulmonary emphysema, organ dysfunction after surgical operation, organ dysfunction after radiotherapy, nephritis, nephrotic syndrome, acute renal failure, haemodialysis, extracorporeal circulation, artificial breathing, acute/chronic rejection after organ transplantation, SLE, rheumatoid arthritis, DIC, autoimmune disease group, Behcet's disease, myocarditis, endocarditis, ischemia reperfusion disorder, myocardial infarction, congestive heart failure, adipose tissue inflammation, neutrophilic dermatosis, Sweet's disease, Stevens-Johnson syndrome, Reye syndrome, cachexia, chronic fatigue syndrome and fibromyalgia.

13. The treatment method described in the preceding item 11 or 12, wherein the diseases caused by neutrophil activation and/or the inflammatory diseases accompanied by neutrophil activation are diseases selected from sepsis, acute respiratory distress syndrome, acute pancreatitis, and acute pulmonary disorder.

Advantageous Effect of Invention

The neutrophil-vascular endothelial cell interaction can be inhibited by the neutrophil activation regulator comprising the HRG of the present invention as an active ingredient, for example the regulator can be used as a therapeutic agent for the diseases caused by neutrophil activation and/or the inflammatory diseases accompanied by neutrophil activation. Furthermore, an inspection method for diseases caused by neutrophil activation can be provided by measuring the blood HRG level.

BRIEF DESCRIPTION OF DRAWINGS

FIG. 1 Diagrams showing results of purification of the HRG from human plasma by Nickel-nitrilotriacetic acid (Ni-NTA) affinity chromatography (Example 1).

FIG. 2 Diagrams showing results of purification of the HRG from human plasma by anion-exchange chromatography (Example 1).

FIG. 5 A flow chart showing a processing method of the neutrophil for confirming the morphology of the neutrophil (Experimental Example 1-2).

FIG. 11 A graph and a conceptual diagram in observing adhesiveness of the neutrophil to the vascular endothelial cell when the neutrophil was treated with HRG. The positive control is fMLP, and the negative control is HBSS (Experimental Example 1-4).

Figure 3:
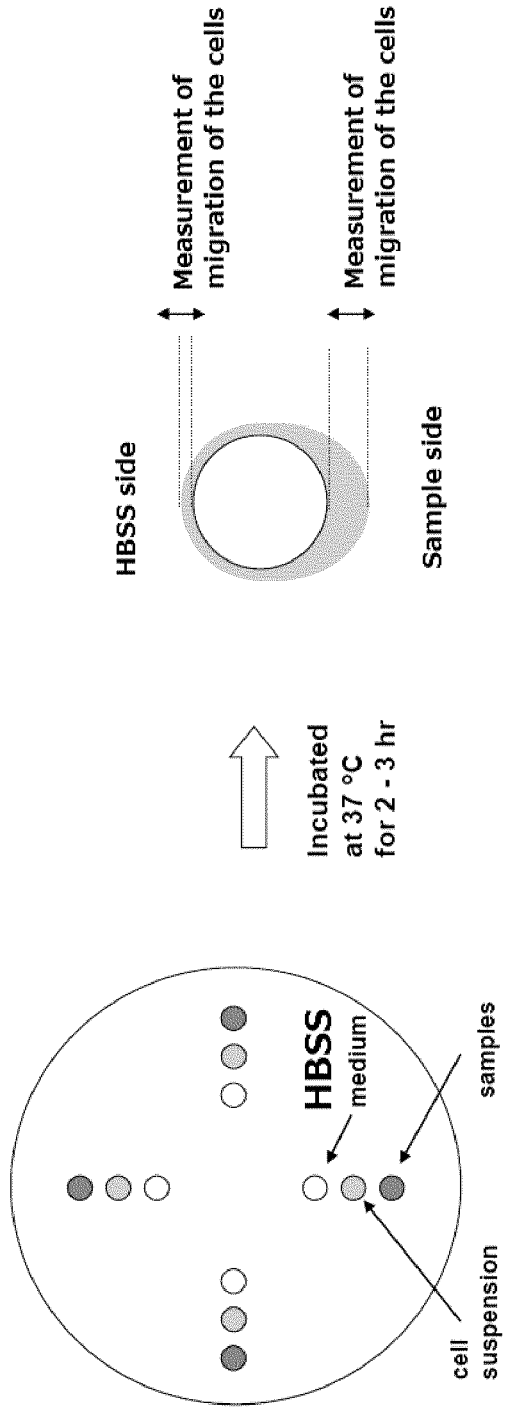
FIG. 3 Diagrams showing an assay method for migration capability of the neutrophil by agarose flat plate (Experimental Example 1-1).

The present invention relates to a neutrophil activation regulator which comprising a HRG (Histidine-rich glycoprotein) as an active ingredient. In the present specification, the "HRG" as an active ingredient can be prepared from biological constituents by a method such as isolation/purification, genetic engineering technique or synthesis.

In the present specification, the HRG can be prepared from biological constituents of blood such as plasma or serum, spinal fluid, lymph, and the like by isolation/purification. Particularly, suitable biological constituents are blood components such as plasma and serum. As to the method for isolating/purifying the HRG from the biological constituents, known per se methods or any methods which will be developed in the future can be applied. For example, the HRG can be isolated/purified by allowing plasma to pass through an affinity column prepared using a Ni-NTA (nickel-nitrilotriacetic acid) agarose resin.

In the present specification, the HRG can also be prepared using a genetic engineering technique. Known per se methods or every method which will be developed in the future can be applied as the method by the genetic engineering technique. A whole-length cDNA encoding the HRG, or a cDNA encoding a site having HRG activity, for example, a whole-length cDNA encoding an amino acid sequence (SEQ ID NO: 1) of a mature HRG or a cDNA encoding its part can also be cloned in an expression vector for preparation. For example, the HRG can also be prepared from the whole or its part of a nucleotide identified in GenBank Accession No. NM000412 by a genetic engineering technique. The HRG as an active ingredient in the present invention may be the whole of the mature HRG, or a partial protein or a peptide having HRG activity in the mature HRG. Furthermore, the HRG may be a HRG with or without a sugar chain.

The amino acid sequence of the mature HRG (SEQ ID NO: 1)

```
VSPTDCSAVEPEAEKALDLINKRRRDGYLFQLLRIADAHLDRVENTTV

YYLVLDVQESDCSVLSRKYWNDCEPPDSRRPSEIVIGQCKVIATRHSH

ESQDLRVIDFNCTTSSVSSALANTKDSPVLIDFFEDTERYRKQANKAL

EKYKEENDDFASERVDRIERVARVRGGEGTGYFVDFSVRNCPRHHFPR

HPNVEGFCRADLEYDVEALDLESPKNLVINCEVFDPQEHENINGVPPH

LGHPFHWGGHERSSTTKPPFKPHGSRDHHHPHKPHEHGPPPPPDERDH

SHGPPLPQGPPPLLPMSCSSCQHATFGTNGAQRHSHNNNSSDLHPHKH

HSHEQHPHGHHPHAHHPHEHDTHRQHPHGHHPHGHHPHGHHPHGHHPH

GHHPHCHDFQDYGPCDPPPHNQGHCCHGHGPPPGHLRRRGPGKGPRPF

HCRQIGSVYRLPPLRKGEVLPLPEANFPSFPLPHHKHPLKPDNQPFPQ

SVSESCPGKFKSGFPQVSMFFTHTFPK
```

After signal peptides are cleaved by a protease, the mature HRG is made up of four main regions: (1) cystatin-like region 1, (2) cystatin-like region 2, (3) His/Pro region and (4) C-terminal region. The His/Pro region is very rich in proline residues and histidine residues, and can be identified by amino acid sequences shown in position 330 to position 389 in the amino acid sequence identified by SEQ ID NO: 1. In another aspect, for example, in a human type, the His/Pro region can also be identified by amino acid sequence including about 12 tandem repeats in which a pentapeptide GHHPH (SEQ ID NO: 2) is preserved.

The "neutrophil activation regulator" of the present invention comprising the above-explained HRG as an active ingredient. The "neutrophil activation regulator" of the present invention can include a HRG obtained by isolation/purification from biological constituents or a HRG obtained by gene recombination as an active ingredient, and additionally a pharmaceutically acceptable carrier. The pharmaceutically acceptable carrier can include, for example, excipient, disintegrator or disintegrating aid, binder, lubricant, coating agent, pigment, diluent, base, solubilizer or solubilizing agent, isotonicifier, pH regulator, stabilizer, propellant, sticker, and the like. The neutrophil activation regulator in the present invention may be a crude product itself obtained from biological constituents by isolation/purification.

The neutrophil activation regulator of the present invention has an action to inhibit neutrophil activity in addition to an action to inhibit neutrophil-vascular endothelial cell interaction. Furthermore, the neutrophil activation regulator can be used for a therapeutic agent for diseases caused by neutrophil activation and/or inflammatory diseases accompanied by neutrophil activation that utilizes actions to inhibit neutrophil activity and to inhibit neutrophil-vascular endothelial cell interaction. Consequently, the present invention extends to the neutrophil-vascular endothelial cell interaction depressant agent including the neutrophil activation regulator and to the therapeutic agent for diseases caused by neutrophil activation and/or inflammatory diseases accompanied by neutrophil activation.

The present invention also extends to a treatment method for diseases caused by neutrophil activation and/or inflammatory diseases accompanied by neutrophil activation, characterized in that the neutrophil activation regulator comprising the HRG as an active ingredient is used.

The "diseases caused by neutrophil activation and/or inflammatory diseases accompanied by neutrophil activation" in the present specification may be literally any diseases caused by neutrophil activation and/or any inflammatory diseases accompanied by neutrophil activation, and include, but are not especially limited to, one or a plurality of diseases selected from, for example, sepsis, acute respiratory distress syndrome, acute pancreatitis, acute pulmonary disorder, pulmonary disorder caused by the hemorrhagic shock, multiple organ failure, burn, multiple injury, idiopathic interstitial pulmonary fibrosis, cerebral trauma, spinal cord injury, neuropathic pain, cerebral infarction, cerebral vasospasm after the subarachnoid hemorrhage, epilepsy, status epilepticus, viral encephalitis, influenza-associated encephalopathy, inflammatory bowel disease, kawasaki disease, multiple sclerosis, diabetic vascular complication, hepatitis, arteriosclerosis, asthma bronchial, chronic bronchitis, pulmonary emphysema, organ dysfunction after surgical operation, organ dysfunction after radiotherapy, nephritis, nephrotic syndrome, acute renal failure, haemodialysis, extracorporeal circulation, artificial breathing, acute/chronic rejection after organ transplantation, SLE, rheumatoid arthritis, DIC, autoimmune disease group, Behcet's disease, myocarditis, endocarditis, ischemia reperfusion disorder, myocardial infarction, congestive heart failure, adipose tissue inflammation, neutrophilic dermatosis, Sweet's disease, Stevens-Johnson syndrome, Reye syndrome, cachexia, chronic fatigue syndrome and fibromyalgia. Particularly, the diseases include suitably any diseases selected from sepsis, acute respiratory distress syndrome, and acute pancreatitis.

The "neutrophil-vascular endothelial cell interaction depressant agent" or "therapeutic agent for diseases caused by neutrophil activation and/or inflammatory diseases accompanied by neutrophil activation" of the present invention may be locally or systemically administered. A parenteral formulation may include a sterilized aqueous or non-aqueous solution, suspension and emulsion. Examples of non-aqueous diluent may include propylene glycol, polyethylene glycol, vegetable oil, for example, olive oil and organic ester composition, for example, ethyl oleate, and they are suitable for injection. Aqueous carriers may include water, alcoholic aqueous solution, emulsion, suspension, salt water and buffered medium. Non-aqueous carriers may include sodium chloride solution, Ringer dextrose, dextrose and sodium chloride, Ringer lactic acid and binding oil. Intravenous carrier may include, for example, filler for liquid, nutrition and electrolyte (based on, for example, Ringer dextrose). The therapeutic agent of the present invention for diseases caused by neutrophil activation and/or inflammatory diseases accompanied by neutrophil activation can further include a preservative and other additives, for example, an antimicrobial compound, an antioxidant, a chelating agent, an inert gas, and the like.

The "depressant agent for neutrophil-vascular endothelial cell interaction" or the "therapeutic agent for diseases caused by neutrophil activation and/or inflammatory diseases accompanied by neutrophil activation" of the present invention may be used in combination with other drugs. For example, an anti-HMGB1 monoclonal antibody described in a brochure of WO/2012/074043 can also be combined for use.

Furthermore, the present invention extends to an inspection method for diseases caused by neutrophil activation and/or inflammatory diseases accompanied by neutrophil activation, which is characterized in that a blood HRG level is measured. In the case of diseases caused by neutrophil activation and/or inflammatory diseases accompanied by neutrophil activation, it is recognized that the blood HRG level is inclined to be lower than the normal level. Specific examples of the diseases caused by neutrophil activation and/or the inflammatory diseases accompanied by neutrophil activation are as mentioned above.

The measurement method of the blood HRG level may be any method enabling quantitative measurement, and the level can be measured by e.g., but not particularly limited to, immunological procedure. The immunological procedure includes measurement methods using anti-HRG antibodies, and more specifically includes an antibody sandwich ELISA (Enzyme-Linked ImmunoSorbent Assay) method, an antibody/NiNTA-HRP probe sandwich ELISA method, an ELISA method using chemoluminescence for detection, a latex agglutination method, a western blot method, and the like. As a test sample subjected to these measurement methods, a sample in which a specimen obtained through blood collection by known per se method is prepared by a preparation method for conventional clinical test samples can be used. More specifically, a plasma sample prepared by, for example, a preparation method for conventional clinical test samples can be used as a test sample.

EXAMPLES

Hereinafter, the present invention will be specifically explained by Examples and Experimental Examples. Basically, the present invention is not limited by the following Examples and the like, and can be carried out with appropriate modifications within the scope that can be adapted to the gist of the present invention, and any of the modifications are incorporated in the technical scope of the present invention.

Example 1

Preparation of Neutrophil Activation Regulator

In this Example, preparation of the neutrophil activation regulator including the HRG as an active ingredient will be explained.

In this Example, a human plasma (240 ml) was used as a starting material, and the HRG was purified by Ni-NTA (nickel-nitrilotriacetic acid) affinity chromatography and high-performance liquid chromatography (anion-exchange column (monodisperse hydrophilic polymer beads: Mono Q)). A purification pattern from the human plasma is shown in FIG. 1 and FIG. 2. Thereby, a HRG purification sample was obtained in a fraction of molecular weight of about 80 kDa. The purified sample was dialyzed by a phosphate buffered saline (1×PBS (−)), and the preparation containing 500-1000 μg/ml (5 ml) of HRG was stored as the neutrophil activation regulator of the present invention. For the experiment, the concentration of the HRG was adjusted by Hank's balanced salt solutions (HBSS) for use.

Experimental Example 1-1

Confirmation of Chemotaxis by Agarose Flat Plate

The chemotaxis of the neutrophil in a horizontal state by the neutrophil activation regulator (HRG: 1 μM) prepared in Example 1 was confirmed. In this Experimental Example, an HBSS containing $5×10^6$ cell/ml of neutrophil prepared from human peripheral blood was used as a neutrophil suspension. An HBSS containing 1 μM of bovine serum albumin (BSA) was used as a negative control, and an HBSS containing 1 μM of fMLP (bacteria-derived migratory factor: N-formyl-methionyl-leucyl-phenylalanine) was used as a positive control.

Figure 4A:
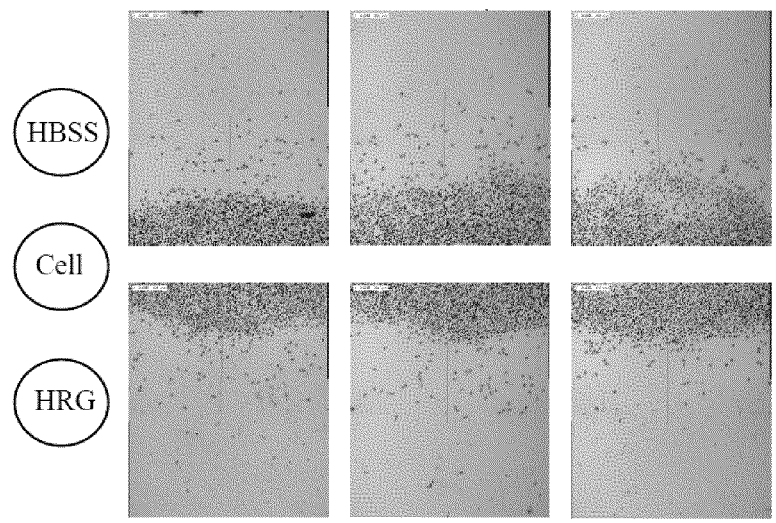
FIG. 4A Photographs taken in confirming migration capability of the neutrophil with HRG by agarose flat plate (Experimental Example 1-1).
Figure 4B:
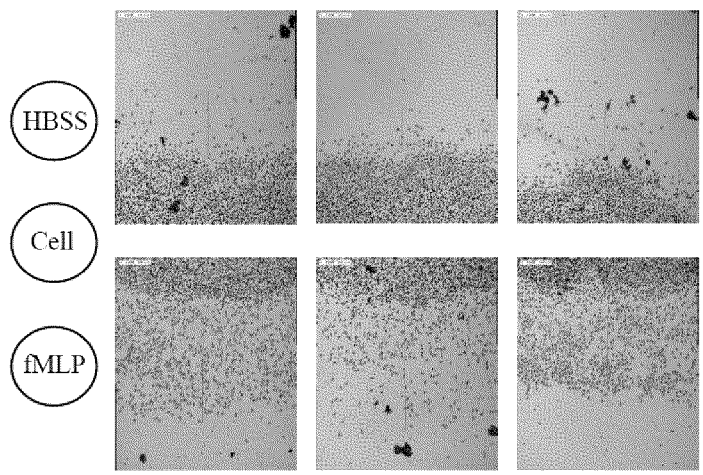
FIG. 4B Photographs taken in confirming migration capability of the neutrophil with fMLP (positive control) by agarose flat plate (Experimental Example 1-1).
Figure 4C:
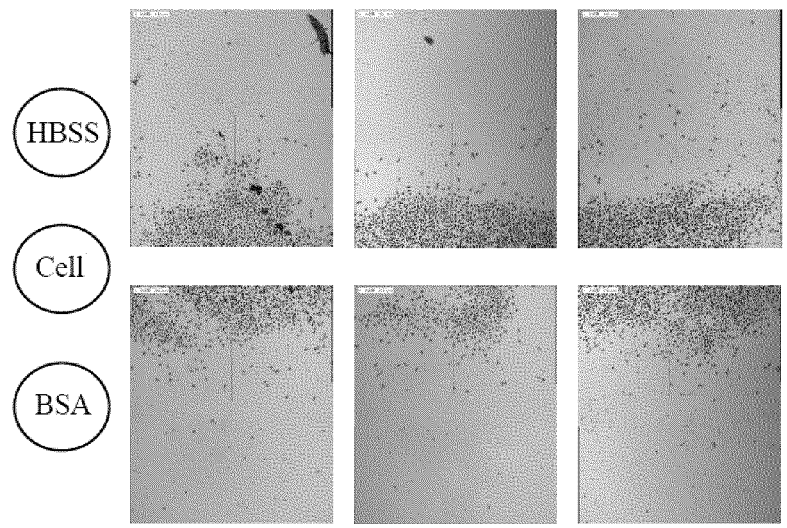
FIG. 4C Photographs taken in confirming migration capability of the neutrophil with BSA (bovine serum albumin: negative control) by agarose flat plate. (Experimental Example 1-1).

Three holes with 3 mm of diameter are provided on the agarose flat plate as shown in FIG. 3, 10 μl of HBSS was added in one hole, 10 μl of sample solution (sample) like a neutrophil activation regulator was added on the other hole, and 10 μl of neutrophil suspension was added on the middle hole. They were cultured at 37° C. for 3 hours, and migration of cells was confirmed. As a result, the system with the neutrophil activation regulator (HRG) showed no migration of neutrophil like the system of the negative control (BSA) (FIG. 4C), as shown in FIG. 4A.

Experimental Example 1-2

Morphology of Neutrophil

Figure 6:
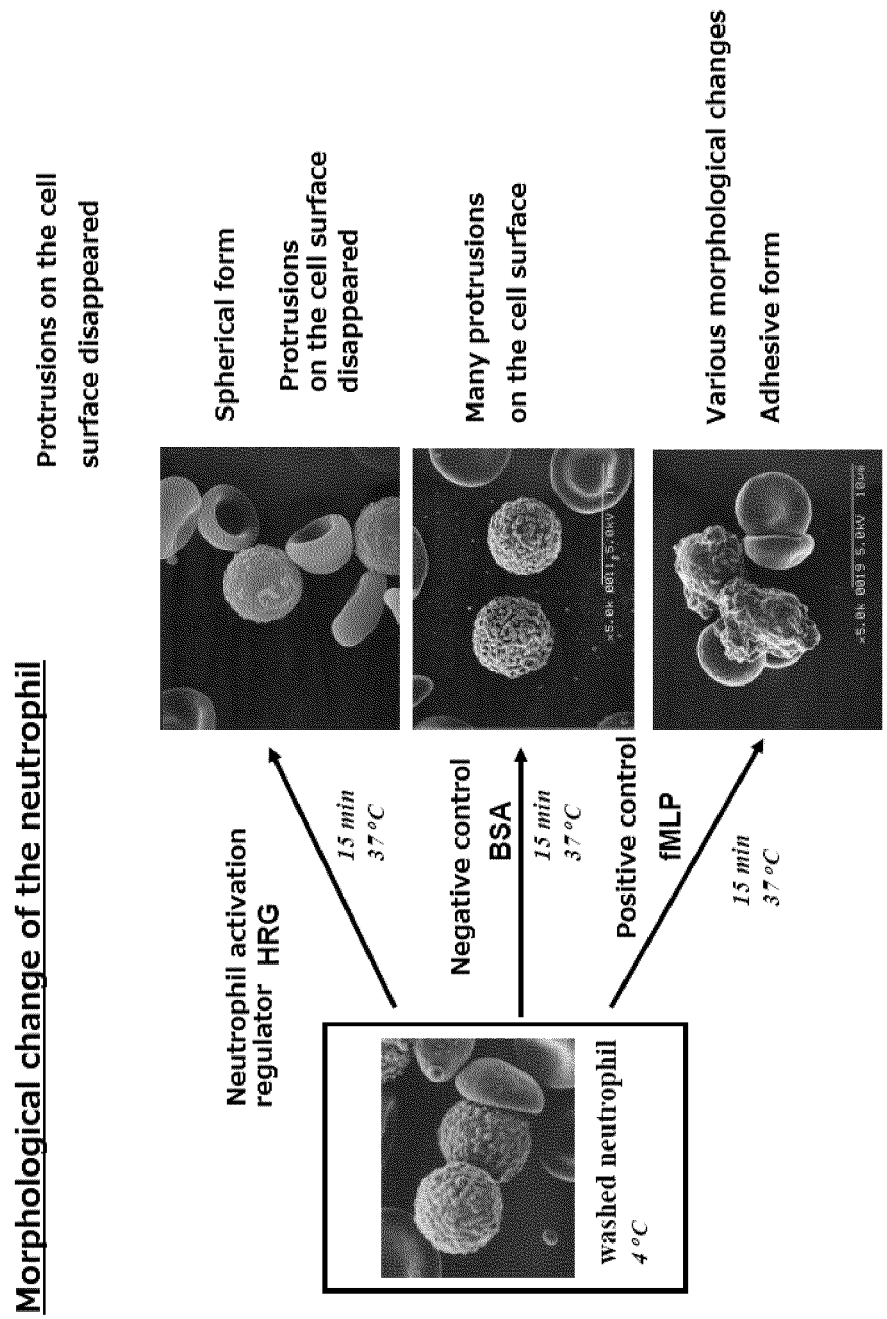
FIG. 6 Photographs taken in observing morphology of the neutrophil treated with HRG by an electron microscope. The positive control is fMLP, and the negative control is BSA (Experimental Example 1-2).

According to the flow chart shown in FIG. 5, the morphology of the neutrophil in the system in which 50 μl of neutrophil activation regulator prepared in Example 1 (HRG: 2 μM, final concentration: 1 μM) was added to 50 μl of neutrophil suspension prepared by the same procedure as in Experimental Example 1 ($5×10^5$ cell/ml) was observed by an electron microscope. In the same way as in Experimental Example 1, BSA was used as a negative control, and fMLP was used as a positive control. As a result, as shown in FIG. 6, it was observed that the positive control (fMLP) showed various morphological changes and an adhesive form, whereas the system with the neutrophil activation regulator (HRG) showed a more spherical state than that in the negative control (BSA). Also in the case of the negative control, many micro-villous protrusions appeared on the cell surface, and this was considered to be caused by stimulation by cell treatment, but in the system with neutrophil activation regulator, even when such a stimulation existed, activation of the neutrophil was controlled, and thus it was considered that a low activity state with extremely fewer micro-villous protrusions was able to be maintained.

Figure 7:
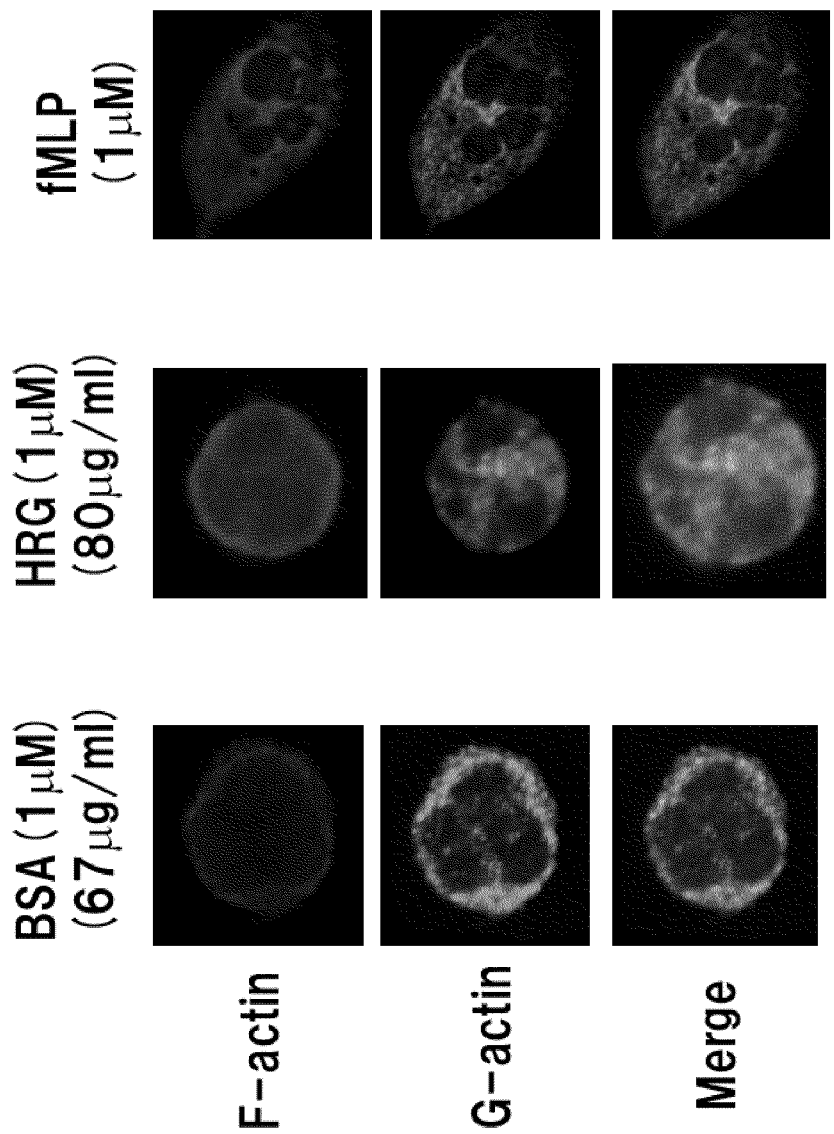
FIG. 7 Views taken in confirming distributions of F-actin and G-actin treated with HRG in neutrophils. The positive control is fMLP, and the negative control is BSA (Experimental Example 1-2).

Next, distributions of polymerized actins (F-actin) and globular actins (G-actin) in cells were observed. The F-actin was stained into red by Alexa Fluor 568-labeled phalloidin, and the G-actin was stained into green by Alexa Fluor 488-labeled deoxyribonuclease I. As a result, as shown in FIG. 7, it was observed that the neutrophil activation arranged the F-actin immediately below a plasma membrane of the cell.

Figure 8:
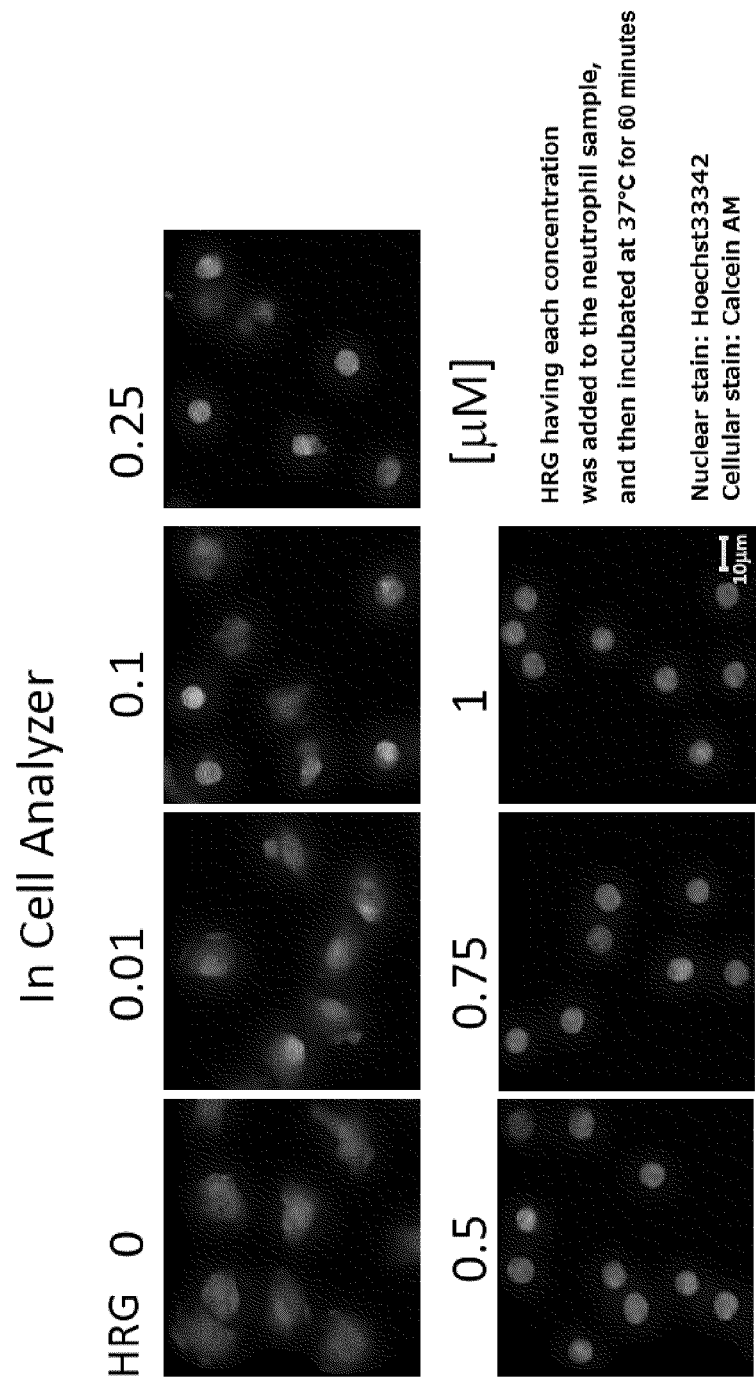
FIG. 8 Photographs taken in observing the morphology of the neutrophil treated with each concentration of HRG by cell fluorescence stain (Experimental Example 1-2).

Subsequently, the shapes of the cells in the system with the neutrophil activation regulator containing each concentration of HRG were confirmed with fluorescent label by using an imaging cytometer. As a result, it was observed that the cells were able to be maintained in a globular shape in a HRG concentration-dependent manner (FIG. 8).

Experimental Example 1-3

Permeability of the Neutrophil Through an Artificial Capillary

Figure 9:
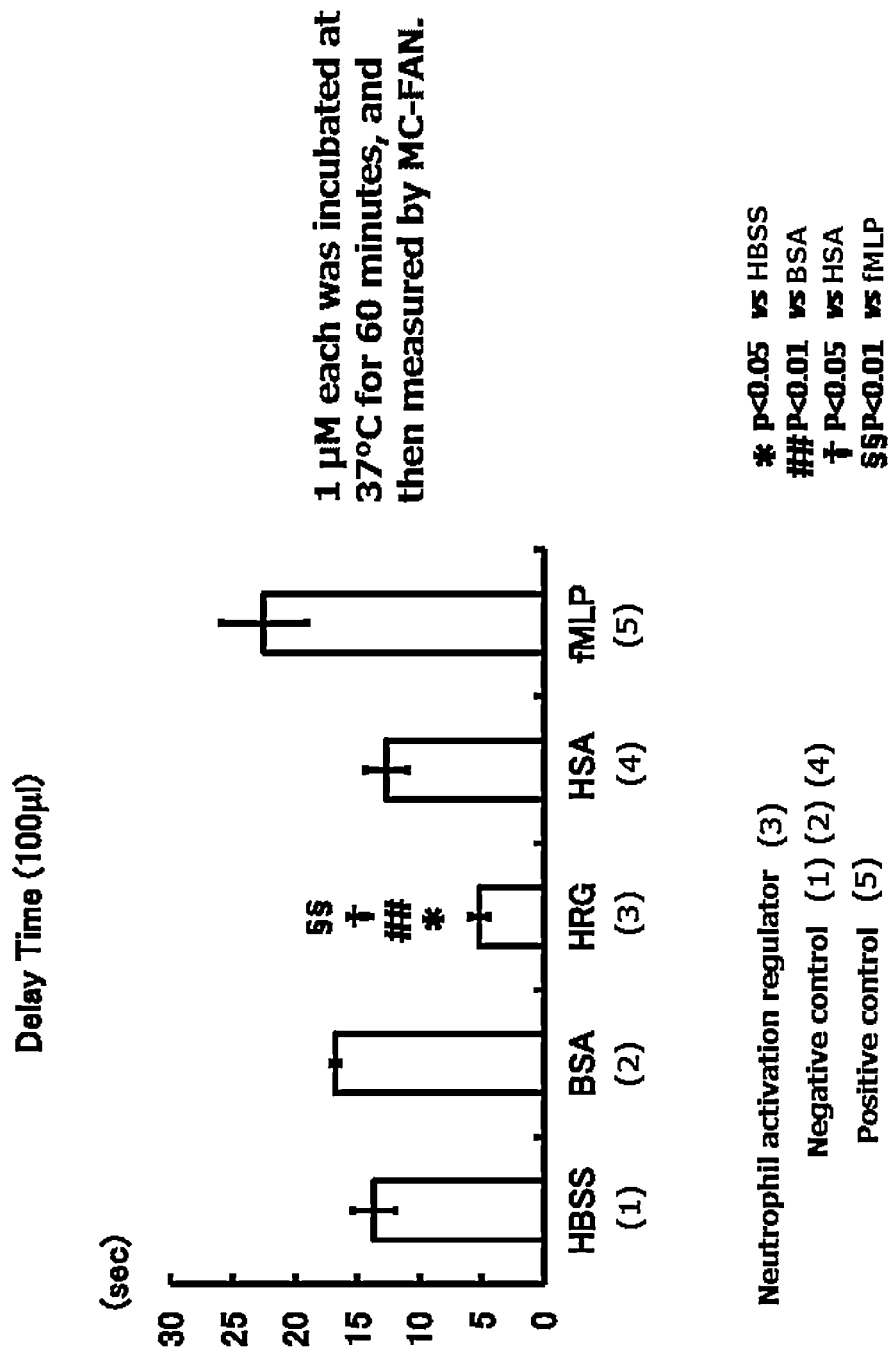
FIG. 9 Diagrams showing results of confirmation of flowability of the neutrophil suspension treated with HRG by MC-FAN. The positive control is fMLP, and the negative controls are BSA and HSA (Experimental Example 1-3).

In this Experimental Example, a permeability of the neutrophil suspension by the neutrophil activation regulator (HRG: final concentration of 1 µM) prepared in Example 1 was measured by MC-FAN (Micro Channel array Flow Analyzer). The system in which the neutrophil activation regulator prepared in Example 1 was added to the neutrophil suspension was incubated at 37° C. for 60 minutes, and then its passage flowability was confirmed through measurement by using an MC-FAN silicon chip. The HBSS, BSA (bovine serum albumin) and HSA (human serum albumin) were used as negative controls, and the fMLP was used as a positive control. As a result, as shown in FIG. 9, the system of the neutrophil activation regulator showed smooth passage as compared with that of the negative control.

Experimental Example 1-4

Adhesiveness of the Neutrophil

Figure 10:
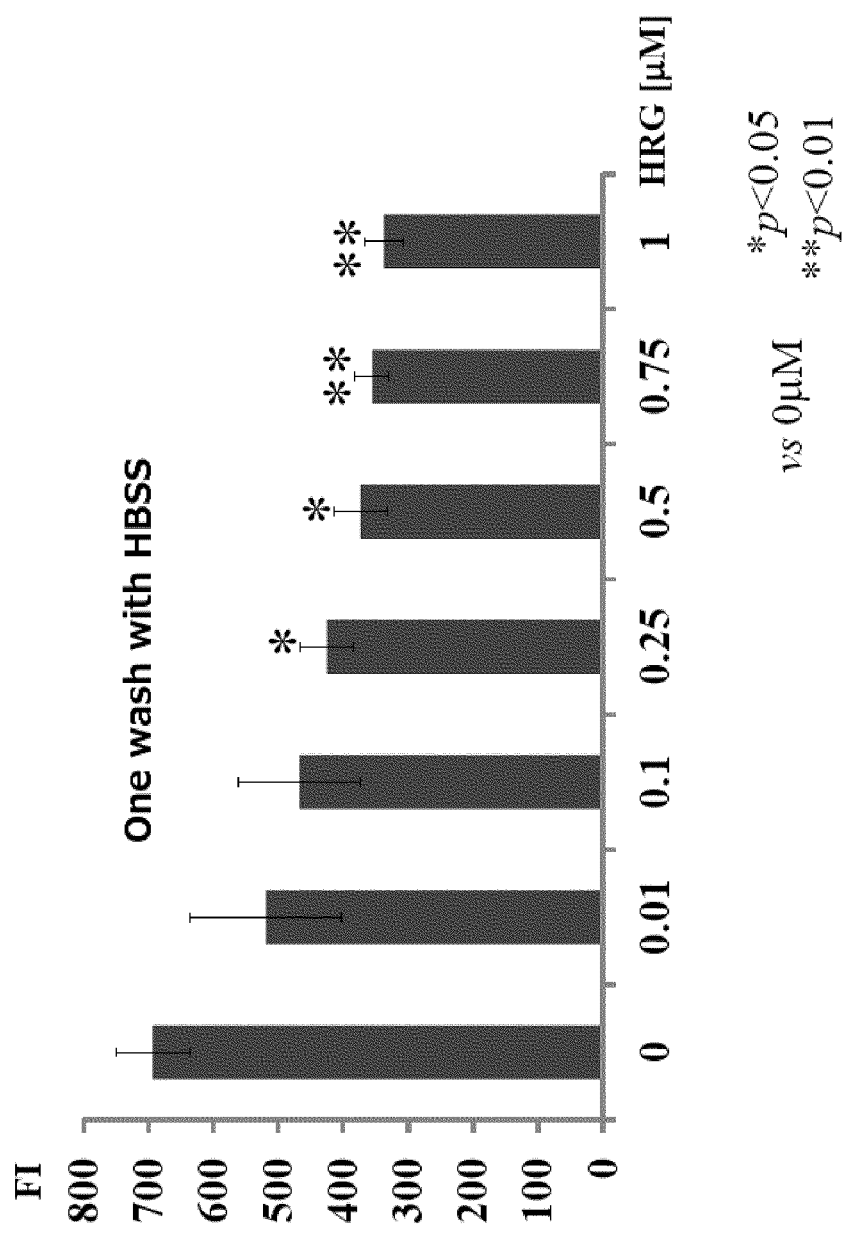
FIG. 10 Results of the number of the adherent cells in observing adhesion of the neutrophil to a microplate when the neutrophil was treated with each concentration of HRG (Experimental Example 1-4).

In this Experimental Example, after the neutrophil activation regulator containing each concentration of HRG prepared in Example 1 was added to the neutrophil suspension and incubated at 37° C. for 60 minutes, the adhesiveness of the neutrophil in the microplate was measured using the imaging cytometer. As a result, as shown in FIG. 10, it was confirmed that the system of the neutrophil activation regulator decreased the cell adhesiveness in a HRG concentration-dependent manner.

After that, the adhesiveness of the neutrophil to a human umbilical vein endothelial cell (HUVEC) was measured using the imaging cytometer. As a result, as shown in FIG. 11, it was confirmed that, in the system with the neutrophil activation regulator, the cell adhesiveness was maintained lower than that in the negative control.

Example 2

Effects of the HRG on CLP Sepsis Model Mice

1. Change of the Blood HRG Level in CLP Model Mice

In this Experimental Example, HRG kinetics was examined through the use of sepsis models with cecal ligation and puncture (CLP). A cecum was excised from an abdominal cavity of the mouse, the root of the cecum was ligated with a suture, and the layer of the cecal wall was punctured using an 18-gauge needle to produce a CLP sepsis model. A sham mouse was used a control. In relation to the blood HRG level in the living body, the plasma was subjected to SDS-PAGE electrophoresis, then transcribed on a nylon membrane, and detected by western blotting for measurement.

Figure 12:
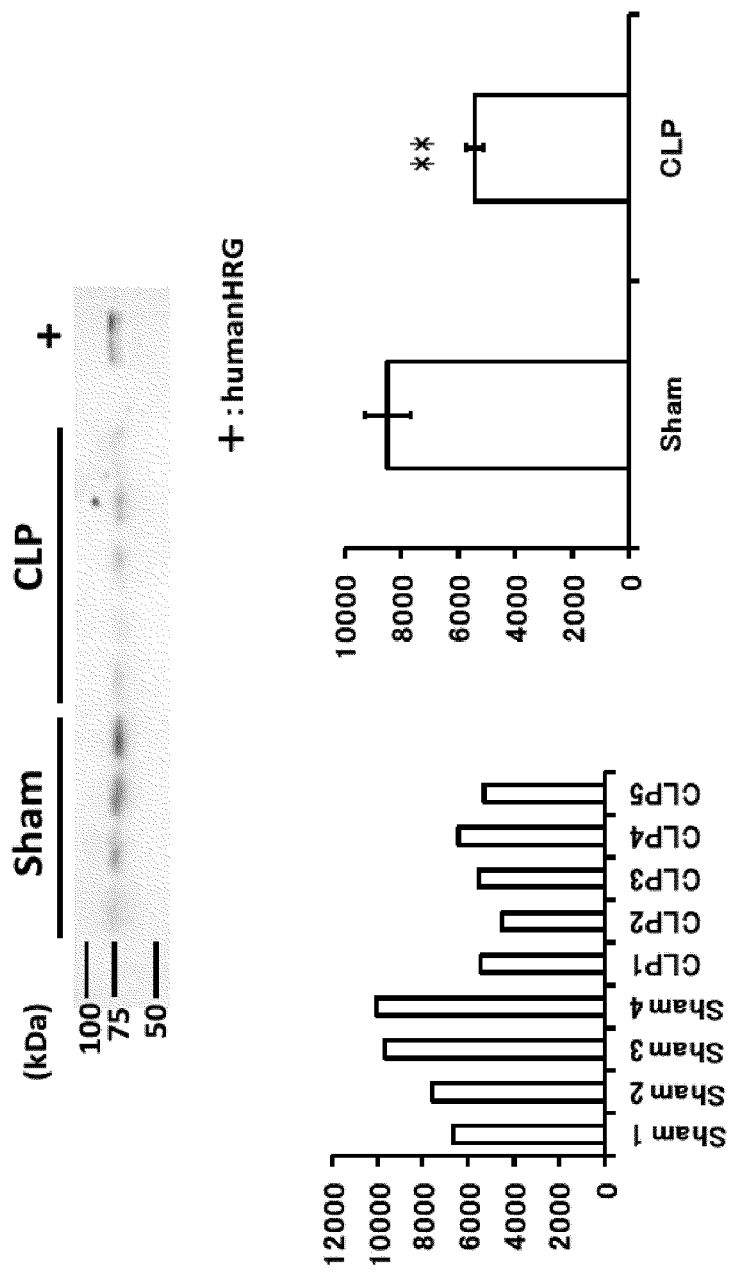
FIG. 12 Diagrams of results obtained by confirming the HRG kinetics in CLP sepsis model mice (Example 2).

As a result, it was observed that the HRG of the CLP sepsis model group was significantly decreased as compared with that of the sham group (FIG. 12).

2. Effects of the HRG on the CLP Sepsis Model Mice

In this Example, effects on survival rates of mice when the neutrophil activation regulator prepared in Example 1 was administered to the CLP sepsis model mice produced by the same method as mentioned above were confirmed. The prepared neutrophil activation regulator (HRG: 400 µg/mouse) was administered into caudal vein, 5 minutes, 24 hours and 48 hours after the surgery (n=10). HSA was used as a control (n=10).

Figure 13:
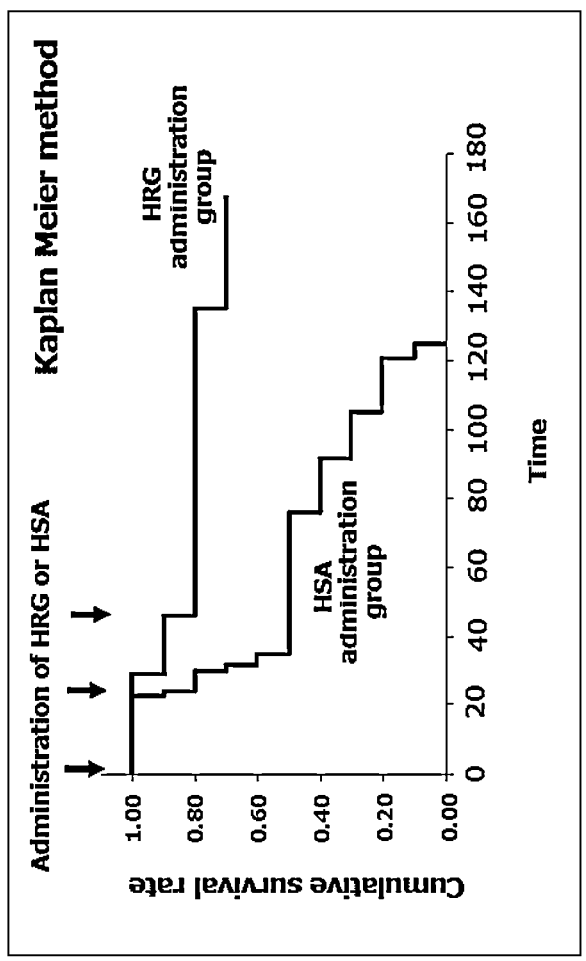
FIG. 13 Diagrams of results obtained by confirming the effects on the survival rates when the HRG was administered to the CLP sepsis model mice. The control is HSA (human serum albumin) (Example 2).

As a result of analysis by Kaplan Meier method, the group of neutrophil activation regulator administration was confirmed to have a significantly higher cumulative survival rate (FIG. 13).

Example 3

Measurement Method for the HRG (Antibody Sandwich ELISA Method)

In this Example, a measurement method of the blood HRG by antibody sandwich ELISA (Enzyme-Linked ImmunoSorbent Assay) method will be explained.

By conventional method, rabbit immune serum immunized with human HRG was purified using Protein A to obtain an anti-human HRG-rabbit polyclonal antibody. For the HRG used in the immunization of the rabbit, a HRG prepared by the same procedure as described in Example 1 was used. To a plate for ELISA, 10 µg/ml (100 al) of antibody solution adjusted with 0.05 M of $Na_2CO_3$ (pH 9.6) was added, and solid-phased at 4° C. for 16 hours. Subsequently, it was blocked with 3% BSA.

In this Example, an autogenous human HRG protein standard solution (native human HRG protein standard solution) made by the same procedure as in Example 1 was confirmed as a sample. Each concentration of native human HRG protein standard solution of 100 µl, which was 200-500-fold diluted with Tris-Buffered Saline (TBS), was added and incubated at 37° C. for 2 hours. The plate for ELISA was washed with TBS, then 100 µl of HRP-labeled anti HRG-rat polyclonal antibody (clone #75-14) (0.25 µg/ml) was added, incubated at 37° C. for 1.5 hours. The plate for ELISA was washed with TBS, then ortho-phthalenediamine and $H_2O_2$ were added as substrates, chromogenic reaction was carried out for 30 minutes, then the reaction was terminated with 50 µl of 3M $H_2SO_4$, and an absorbance at 492 nm was measured.

Figure 14:
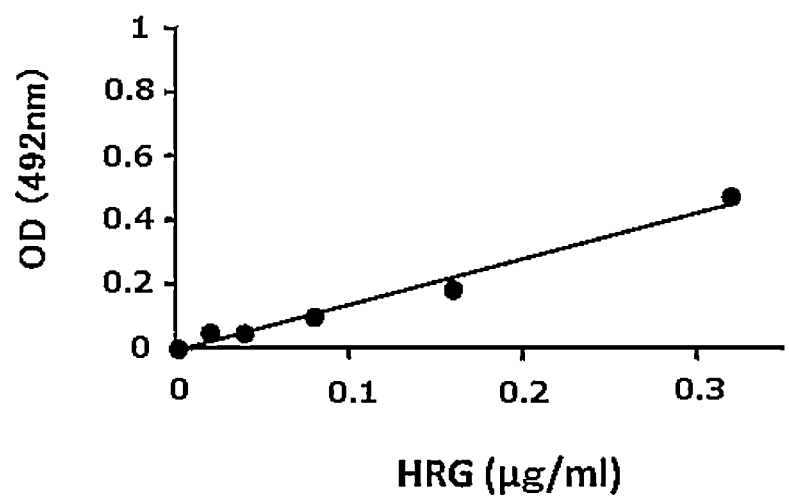
FIG. 14 A diagram showing results of measurement of a standard product (native human HRG protein standard solution) by an antibody sandwich ELISA method (Example 3).

The result of measurement for the native human HRG protein standard solution measured by the above-mentioned method is shown in FIG. 14.

Example 4

Measurement Method for the HRG (Antibody/NiNTA-HRP Probe Sandwich ELISA Method)

In this Example, a measurement method for the blood HRG by an antibody/NiNTA-HRP probe sandwich ELISA method will be explained.

In this method, the rat monoclonal antibody (clone #75-14) was used as an antibody for capturing antigens. To the plate for ELISA, 10 µg/ml (100 µl) of monoclonal antibody solution adjusted with 0.05 M $Na_2CO_3$ (pH 9.6) was added, and solid-phased. Subsequently, it was blocked with 3% BSA, then each concentration of native human HRG protein standard solution of 100 µl, which was 200-500-fold diluted with TBS like in Experimental Example 3, was added and incubated at 37° C. for 2 hours. The plate was washed, then 100 µl of NiNTA-HRP probe (QUIAGEN Cat no. 34530, Tokyo, Japan) (0.25 µg/ml) was added, and incubated at 37° C. for 1.5 hours. The plate was washed, then ortho-phthalenediamine and $H_2O_2$ were added as substrates, chromogenic reaction was carried out for 30 minutes, then the reaction was terminated with 50 µl of 3M $H_2SO_4$, and an absorbance at 492 nm was measured.

Figure 15:
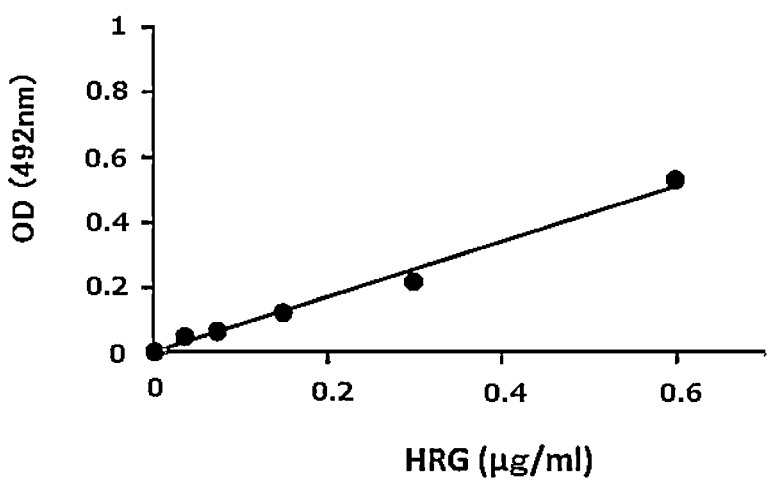
FIG. 15 A diagram showing results of measurement of a standard product (native human HRG protein standard solution) by an antibody/NiNTA-HRP probe sandwich ELISA method (Example 4).

The result of measurement for the native human HRG protein standard solution measured by the above-mentioned method is shown in FIG. 15.

Example 5

Measurement Method for the HRG (Western Blot Method)

In this Example, a measurement method for the blood HRG by a western blot method will be explained. For the blood HRG, a collected human blood was added to a test tube with EDTA, a protease inhibitor cocktail (Sigma, P8340) was added to plasma obtained by centrifugation, and then measured as a sample for electrophoresis. Said adjusted plasma was subjected to SDS-PAGE according to a conventional method, and transcribed on a nitrocellulose membrane. The nitrocellulose membrane was blocked with 3% skim milk, and then reacted with the anti-human HRG-rabbit polyclonal antibody (2 µg/ml) as a primary antibody prepared by the same procedure as in Example 3 at 4° C. for 16 hours. The nitrocellulose membrane was washed, then 1 µg/ml of HRP-labeled anti rabbit IgG goat IgG was added as secondary antibody, and incubated at 37° C. for 1 hour. The nitrocellulose membrane was washed, then luminous reaction was carried out using Super Signal® West Dura Extended Duration Substrate (Thermo Scientific) as a substrate, and the HRG was detected by Lumino Image Analyzer (Image Quant Las 4000 mini, GE healthcare).

Example 6

Blood HRG Level in Human Patients with Sepsis, Patients after Esophageal Cancer Surgery and Healthy Persons For plasma obtained from human patients with sepsis (3 persons), patients after esophageal cancer surgery (4 persons) and healthy persons (4 persons), the blood HRG was measured by the ELISA method described in Example 4 and the western blot method described in Example 5. Each plasma was prepared according to the method described in Example 5.

Figure 16:
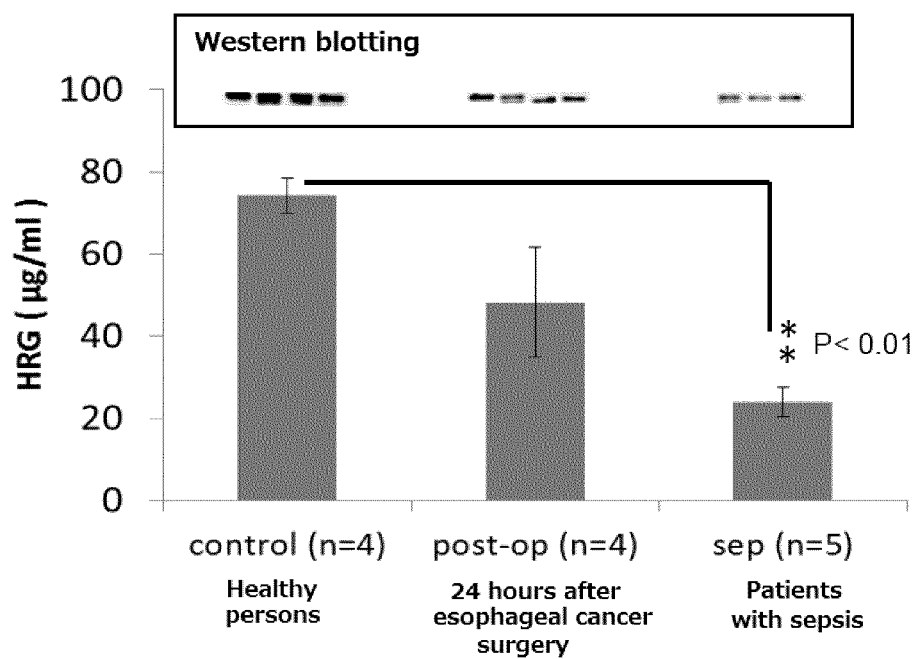
FIG. 16 A diagram showing results of western blotting and ELISA measurement for the blood HRG level in human patients with sepsis, patients after esophageal cancer surgery and healthy persons (Example 6).

Results of measurements are shown in FIG. 16. The results of measurement by the ELISA method are represented by a bar graph, and images of bands obtained by the western blot method are shown above the bar graph. As a result, the results of measurements by the western blotting and the ELISA method exhibited substantially the same result, and in the patients with sepsis, the blood HRG was confirmed to be significantly decreased as compared with that of the healthy persons.

Example 7

Time Course of the Blood HRG in Acute Pancreatitis-ARDS Model Mice

In this Example, time courses of the blood HRG in model mice with acute pancreatitis due to caerulein and subsequent ARDS (acute respiratory distress syndrome) were confirmed. For causing acute pancreatitis and ARDS, mice (body weight 25-30 g) were intravenously injected with 100 µg/dose of caerulein seven times at intervals of one hour to produce model mice. Blood was collected with time after administration of caerulein, the HRG was measured for plasma prepared by the procedure in Example 5 by the western blot method.

Figure 17:
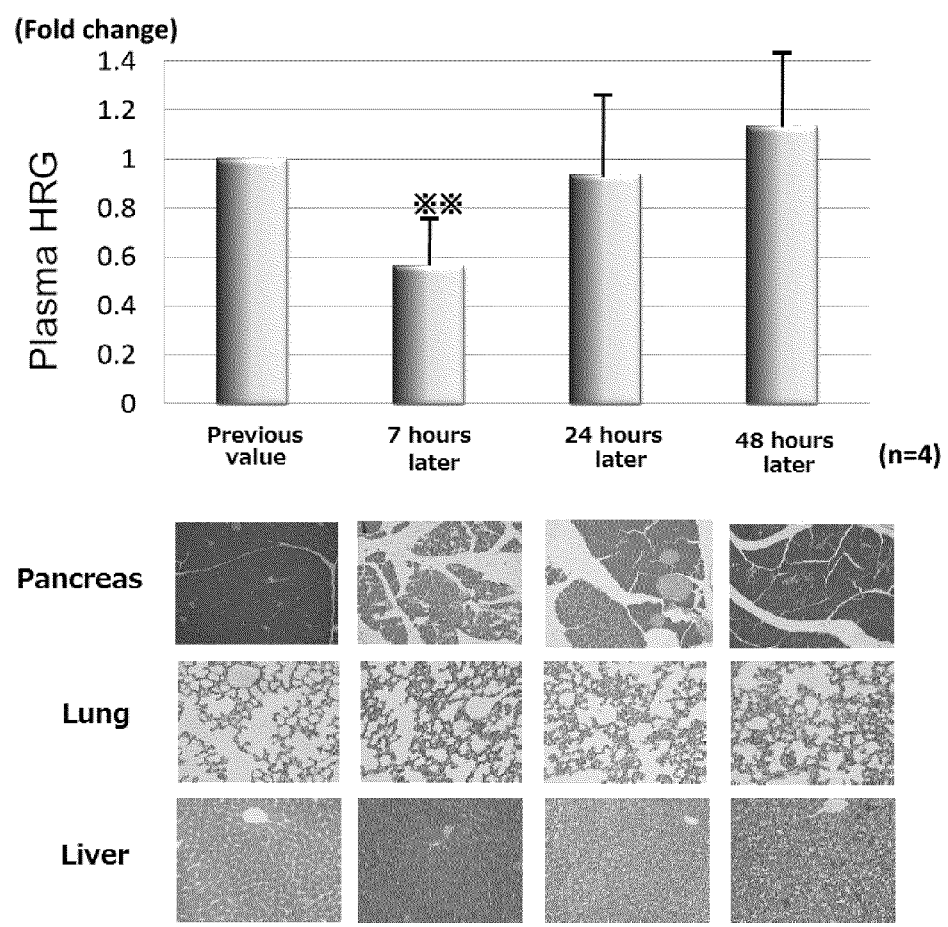
FIG. 17 Diagrams showing time course of the blood HRG and tissue images of pancreas, lung and liver after each lapse of time in acute pancreatitis-ARDS model mice. (Example 7)

Results of measurement are shown in FIG. 17. Also in the mouse acute pancreatitis-ARDS models, the blood HRG was confirmed to be significantly decreased like the mouse sepsis models in Example 2 and the human sepsis patients in Example 6. Furthermore, the tissue images of pancreas, lung and liver after each lapse of time were also confirmed. The blood HRG level was significantly decreased immediately after 7 administrations of caerulein (7 hours later), and recovery was achieved in 24 hours. The inflammation accompanied by edema of pancreas tissue stroma was most intense 7 hours later, and turned into recovery in 48 hours. The inflammation of lung was considered to be ARDS following pancreatitis, and persisted for 7 to 48 hours. In the liver, 24 hours later, vacuolization became remarkable, but 48 hours later, it was partially recovered.

Example 8

Evaluation of Pneumonia and Effects of HRG Treatment in Sepsis-ARDS Model Mice

In this Example, in relation to the model mice produced with CLP by the same procedure as described in Example 2, each pathology of ARDS when the neutrophil activation regulator (HRG) prepared in Example 1 was administrated was evaluated 24 hours after the surgery.

In mice that underwent deep anesthesia by intraperitoneal administration of pentobarbital, blood was removed in a transcardiac manner, systemic perfusion with saline was carried out, then lung tissues were excised, and whole RNA was extracted. A cDNA was synthesized by a reverse transcriptase, and then through the use of this as a template, mRNA expression of the following 5 inflammation-associated genes (TNF-a, PAI-1, Neutrophil elastase, IL-6, iNOS) and GAPDH was quantified and evaluated by Real-time PCR.

Figure 18:
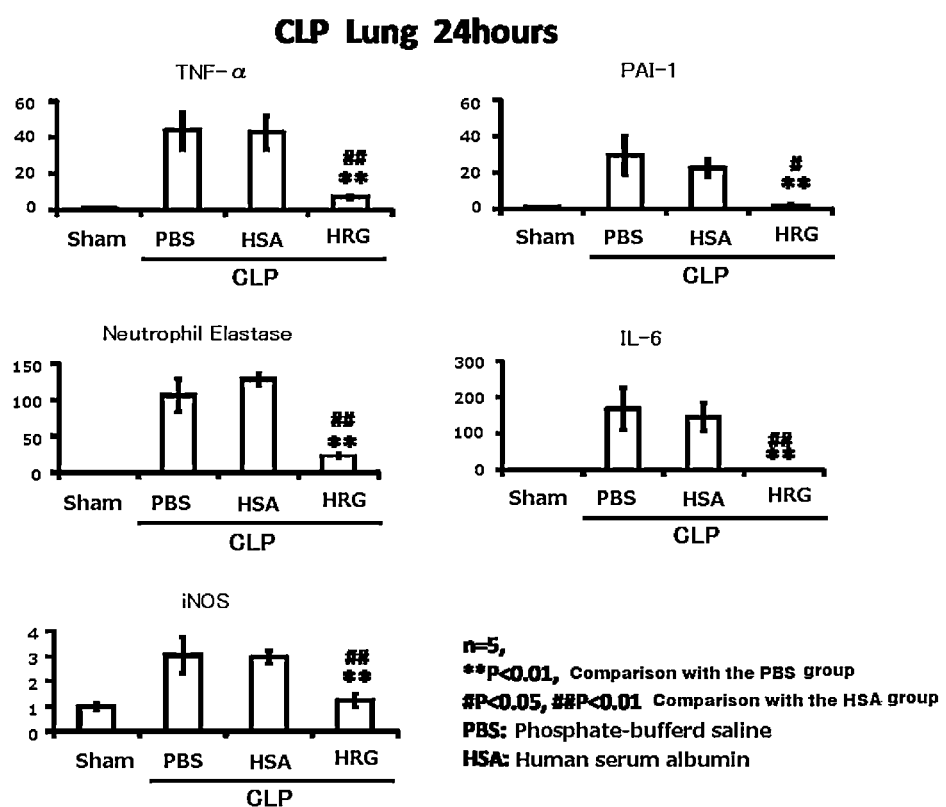
FIG. 18 Diagrams showing results of expressions of five inflammation-associated genes in lung tissues of sepsis-ARDS model mice. (Example 8)

Results of measurement are shown in FIG. 18. Although all expressions of the 5 genes in lung tissues of the sepsis-ARDS model mice were remarkably increased, it was confirmed that all the increased expressions were significantly inhibited by intravenous administration of 1.6 mg/kg of HRG. These results indicate considerable effectiveness of the HRG administration on septic ARDS.

Example 9

Morphology of the Neutrophil in a Case of Treatment with a Recombinant Human HRG In this Example, effects on the morphology of the neutrophil in a case of treatment with the neutrophil activation regulator including a recombinant human HRG produced by a gene recombination procedure as an active ingredient will be explained.

1. Preparation of the Neutrophil Activation Regulator Including the Recombinant Human HRG as an Active Ingredient The recombinant human HRG was produced as below. A DNA encoding a human HRG-coding region (DNA made up of base sequences identified by GenBank Accession No. NM000412) was ligated into a plasmid vector having CMV promoter to prepare a vector for producing a recombinant human HRG. HEK293 cell (derived from human embryonic kidney cell, a transformant caused by adenovirus type 5) was seeded on a cell culture dish with $3.5 \times 10^6$ cells/10 cm diameter, and cultured. The cultured HEK293 cell was removed by a scraper, suspended, then a mixture of the vector for producing the recombinant human HRG 25 μg/OPTI-MEM 500 μl+FuGENE-HD 50 μl/OPTI-MEM 500 μl was added, and reacted at room temperature for 15 minutes for transfection. Subsequently, HEK293 cell was cultured at 37° C. under 5% $CO_2$ for 48 hours to produce the recombinant human HRG.

A culture supernatant containing the recombinant human HRG was collected, and filtrated by a filter with a pore size of 0.22 μm. QIAGEN® Ni-NTA agarose gel (gel in which Ni-NTA binds to Sepharose CL-6B support) previously washed with 30 ml of 1×PBS (−) was added to said filtrated culture supernatant and incubated while rotating at 4° C. for 1 hour to combine the recombinant human HRG to QIAGEN® Ni-NTA agarose gel. QIAGEN® Ni-NTA agarose gel was transferred to a purification column, and then the column was washed with a wash fluid 1 (PBS containing 30 mM Imidazole (pH 7.4)), a wash fluid 2 (1M NaCl+10 mM PBS (pH 7.4)) and a wash fluid 3 (1×PBS (pH 7.4)) sequentially. The recombinant human HRG was eluted by reaction with PBS containing 500 mM Imidazole (pH 7.4) at 4° C. for 1 hour. In the purified product, the HRG was confirmed by western blotting and protein stain after SDS-PAGE.

2. Morphology of the Neutrophil

Figure 19:
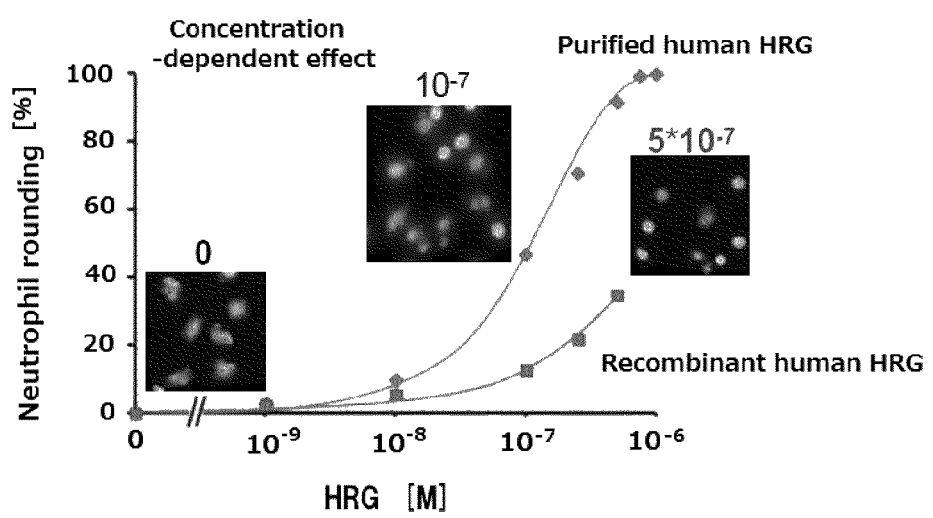
FIG. 19 A diagram showing results obtained by observing the morphology of the neutrophil by a fluorescence microscope and confirming the spherical shape change of the neutrophil when each concentration of recombinant human HRG or human plasma-derived HRG was activated. (Example 9)

A protein concentration was adjusted by HBSS substitution of the recombinant human HRG purified product, and spherical shape-inducing activity of human neutrophil when each concentration of recombinant human HRG was activated was assayed by the same procedure as described in the Experimental Example 1-2. For comparison, the human plasma-derived HRG produced in Example 1 was also confirmed. The results are shown in FIG. 19. Although the activity of the recombinant human HRG was lower than of the human plasma-derived HRG, it was observed that the cells were able to be maintained in the globular shape in a HRG concentration-dependent manner.

INDUSTRIAL APPLICABILITY

As detailed above, by using the neutrophil activation regulator including the HRG of the present invention as an active ingredient, the neutrophil-vascular endothelial cell interaction can be inhibited, for example, diseases caused by neutrophil activation and/or inflammatory diseases accompanied by neutrophil activation can be treated. In addition, since the diseases caused by neutrophil activation and/or the inflammatory diseases accompanied by neutrophil activation decrease blood HRG level, the diseases caused by neutrophil activation and/or the inflammatory diseases accompanied by neutrophil activation can be tested by measuring the HRG.

The invention claimed is:

1. A method for inhibiting neutrophil activation in a subject in need thereof comprising administering to the subject a neutrophil activation regulator comprising a recombinant histidine-rich glycoprotein as an active ingredient, wherein the neutrophil activation regulator inhibits neutrophil activation, and the recombinant histidine-rich glycoprotein is an exogenous histidine-rich glycoprotein.

2. A method for inhibiting neutrophil-vascular endothelial cell interaction in a subject in need thereof comprising administering to the subject a depressant agent comprising a neutrophil activation regulator comprising a recombinant histidine-rich glycoprotein as an active ingredient, wherein the neutrophil activation regulator inhibits neutrophil-vascular endothelial cell interaction, and the recombinant histidine-rich glycoprotein is an exogenous histidine-rich glycoprotein.

3. A method for manufacturing a therapeutic agent for a disease related to neutrophil activation and/or neutrophil-vascular endothelial cell interaction comprising
formulating a recombinant histidine-rich glycoprotein into a composition for parenteral administration comprising an aqueous or non-aqueous carrier and optionally further comprising an additive comprising one or more of an antimicrobial compound, an antioxidant, a chelating agent, and an inert gas, wherein the recombinant histidine-rich glycoprotein is an exogenous histidine-rich glycoprotein.

4. The method according to claim 3, wherein the disease related to neutrophil activation and/or neutrophil-vascular endothelial cell interaction is one or more of, acute respiratory distress syndrome, acute pancreatitis and acute pulmonary disorder.

5. The method according to claim 1, wherein the neutrophil activation regulator further comprises one or more additional drugs.

6. The method according to claim 5, wherein the drug is an anti-HMGB1 monoclonal antibody.

7. The method according to claim 2, wherein the depressant agent further comprises one or more additional drugs.

8. The method according to claim 7, wherein the drug is an anti-HMGB1 monoclonal antibody.

9. The method according to claim 3, wherein the composition further comprises one or more additional drugs.

10. The method according to claim 9, wherein the drug is an anti-HMGB1 monoclonal antibody.

* * * * *

SEQUENCE LISTING

<160> NUMBER OF SEQ ID NOS: 2

<210> SEQ ID NO 1
<211> LENGTH: 507
<212> TYPE: PRT
<213> ORGANISM: Homo sapiens

<400> SEQUENCE: 1

```
Val Ser Pro Thr Asp Cys Ser Ala Val Glu Pro Glu Ala Glu Lys Ala
1               5                   10                  15

Leu Asp Leu Ile Asn Lys Arg Arg Arg Asp Gly Tyr Leu Phe Gln Leu
            20                  25                  30

Leu Arg Ile Ala Asp Ala His Leu Asp Arg Val Glu Asn Thr Thr Val
        35                  40                  45

Tyr Tyr Leu Val Leu Asp Val Gln Glu Ser Asp Cys Ser Val Leu Ser
    50                  55                  60

Arg Lys Tyr Trp Asn Asp Cys Glu Pro Pro Asp Ser Arg Arg Pro Ser
65                  70                  75                  80

Glu Ile Val Ile Gly Gln Cys Lys Val Ile Ala Thr Arg His Ser His
                85                  90                  95

Glu Ser Gln Asp Leu Arg Val Ile Asp Phe Asn Cys Thr Thr Ser Ser
            100                 105                 110

Val Ser Ser Ala Leu Ala Asn Thr Lys Asp Ser Pro Val Leu Ile Asp
        115                 120                 125

Phe Phe Glu Asp Thr Glu Arg Tyr Arg Lys Gln Ala Asn Lys Ala Leu
    130                 135                 140

Glu Lys Tyr Lys Glu Glu Asn Asp Asp Phe Ala Ser Phe Arg Val Asp
145                 150                 155                 160

Arg Ile Glu Arg Val Ala Arg Val Arg Gly Gly Glu Gly Thr Gly Tyr
                165                 170                 175
```

```
        Phe Val Asp Phe Ser Val Arg Asn Cys Pro Arg His His Phe Pro Arg
                        180                 185                 190

His Pro Asn Val Phe Gly Phe Cys Arg Ala Asp Leu Phe Tyr Asp Val
                    195                 200                 205

Glu Ala Leu Asp Leu Glu Ser Pro Lys Asn Leu Val Ile Asn Cys Glu
        210                 215                 220

Val Phe Asp Pro Gln Glu His Glu Asn Ile Asn Gly Val Pro Pro His
        225                 230                 235                 240

Leu Gly His Pro Phe His Trp Gly Gly His Glu Arg Ser Ser Thr Thr
                        245                 250                 255

Lys Pro Pro Phe Lys Pro His Gly Ser Arg Asp His His Pro His
                    260                 265                 270

Lys Pro His Glu His Gly Pro Pro Pro Asp Glu Arg Asp His
                275                 280                 285

Ser His Gly Pro Pro Leu Pro Gln Gly Pro Pro Leu Leu Pro Met
            290                 295                 300

Ser Cys Ser Ser Cys Gln His Ala Thr Phe Gly Thr Asn Gly Ala Gln
        305                 310                 315                 320

Arg His Ser His Asn Asn Asn Ser Ser Asp Leu His Pro His Lys His
                        325                 330                 335

His Ser His Glu Gln His Pro His Gly His His Pro His Ala His His
                    340                 345                 350

Pro His Glu His Asp Thr His Arg Gln His Pro His Gly His His Pro
                    355                 360                 365

His Gly His His Pro His Gly His His Pro His Gly His His Pro His
                    370                 375                 380

Gly His His Pro His Cys His Asp Phe Gln Asp Tyr Gly Pro Cys Asp
        385                 390                 395                 400

Pro Pro Pro His Asn Gln Gly Cys Cys His Gly His Gly Pro Pro
                        405                 410                 415

Pro Gly His Leu Arg Arg Arg Gly Pro Gly Lys Gly Pro Arg Pro Phe
                    420                 425                 430

His Cys Arg Gln Ile Gly Ser Val Tyr Arg Leu Pro Pro Leu Arg Lys
                    435                 440                 445

Gly Glu Val Leu Pro Leu Pro Glu Ala Asn Phe Pro Ser Phe Pro Leu
        450                 455                 460

Pro His His Lys His Pro Leu Lys Pro Asp Asn Gln Pro Phe Pro Gln
        465                 470                 475                 480

Ser Val Ser Glu Ser Cys Pro Gly Lys Phe Lys Ser Gly Phe Pro Gln
                        485                 490                 495

Val Ser Met Phe Phe Thr His Thr Phe Pro Lys
                        500                 505

<210> SEQ ID NO 2
<211> LENGTH: 5
<212> TYPE: PRT
<213> ORGANISM: Homo sapiens

<400> SEQUENCE: 2

Gly His His Pro His
1               5
```